United States Patent [19]

Drevici et al.

[11] 4,206,245
[45] Jun. 3, 1980

[54] COMPLETE UTILIZATION OF COCOA FRUITS AND PRODUCTS

[76] Inventors: Ulla Drevici; Noe Drevici, both of 2150 Center Ave., Fort Lee, N.J. 07024

[21] Appl. No.: 877,479

[22] Filed: Feb. 13, 1978

Related U.S. Application Data

[60] Continuation of Ser. No. 459,318, Apr. 9, 1974, abandoned, which is a division of Ser. No. 165,496, Jul. 23, 1971, Pat. No. 3,809,778.

[51] Int. Cl.$^2$ .......................... A23G 1/00; A23D 3/00
[52] U.S. Cl. .................................. 426/599; 426/615; 426/654; 426/655; 426/603; 131/17 AC; 131/140 C; 8/115.6; 156/336; 106/205; 424/195
[58] Field of Search ............... 426/631, 615, 655, 654, 426/481, 599, 489, 603, 604; 131/17 AC, 140 C; 8/115.6; 156/336; 106/205; 424/195, 196

[56] References Cited

U.S. PATENT DOCUMENTS

| | | | |
|---|---|---|---|
| 3,396,039 | 8/1968 | Leo et al. | 426/654 |
| 3,480,018 | 11/1969 | Fairchild | 131/140 C |
| 3,809,778 | 5/1974 | Drevici et al. | 426/615 |

FOREIGN PATENT DOCUMENTS 1902403  1/1969  Fed. Rep. of Germany .......... 426/631

OTHER PUBLICATIONS

Feeds and Feeding, Morrison 22nd Ed. 1957 Morrison Pub. Co. Ithaca, N.Y.

*Primary Examiner*—Hiram H. Bernstein
*Attorney, Agent, or Firm*—Erich M. H. Radde

[57] ABSTRACT

Valuable products are obtained from Theobroma fruits by preferably removing the peels from said fruits, opening the fruits, separating the seeds from the preferably peeled parenchymatous part of the fruits, and immediately thereafter fermenting the seeds and processing said parenchymatous part. Preferably the fruits are pretreated, for instance, with an alkaline solution and, after peeling, are neutralized, or they are pretreated with a preserving agent. The parenchymatous part of the fruits is expressed to yield the fruit flesh juice containing a hydrocolloid which has proved to be a valuable emulsifying, thickening, stabilizing, suspending agent and protective colloid. The expressed Theobroma fruit flesh is converted into a nutritious animal feed, especially for small animals. Thus the Theobroma fruits are substantially completely utilized.

7 Claims, No Drawings

COMPLETE UTILIZATION OF COCOA FRUITS AND PRODUCTS

CROSS-REFERENCES TO RELATED APPLICATIONS

The present application is a continuation of application Ser. No. 459,318, filed Apr. 9, 1974, now abandoned, and entitled "COMPLETE UTILIZATION OF COCOA FRUITS AND PRODUCTS", which application, in turn, is a division of application Ser. No. 165,496, filed July 23, 1971, and entitled "PROCESS FOR THE COMPLETE UTILIZATION OF COCOA FRUITS", now U.S. Pat. No. 3,809,778.

BACKGROUND OF THE INVENTION (1) Field of the Invention

The present invention is concerned with the utilization of the cocoa fruit and more particularly with its complete utilization with the purpose of producing valuable products such as novel, highly nutritious, salubrious, and tasteful feed compositions for domestic animals and especially for small animals such as chicken, rabbits, and others, and to products and feed compositions produced thereby.

(2) Description of the Prior Art

To increase stock-farming and cattle-breeding in tropical countries is of the greatest importance in the fight against malnutrition and hunger and will become of even greater importance due to the enormous increase in the world's population which can be expected within the next decades, especially in underdeveloped countries. To utilize additional acreage for cultivating and growing tuberous plants, grain, and other farm products is one way of increasing the available food supply. Another way is to improve the food value by feeding such farm products to domestic animals. This has the advantage that the resulting food is richer in protein. Its production, however, requires more time and is rather expensive. Access to additional sources of food is such an urgent matter that it is not possible to utilize the newly developed acreage for producing animal feed. Such acreage should better be used for growing and harvesting crops such as cereals which can directly be made available for human consumption. Therefore, in the initial stage of producing more food for the world's population it must be endeavored to provide and utilize to the greatest possible extent agricultural and industrial waste products for feeding cattle and other domestic animals. Especially agricultural waste products which are readily available at present and which usually are obtainable in large amounts and of a uniform quality, should be employed as animal feed. This is of the greatest importance in the tropics where every effort should be made to feed domestic animals with such waste products. Keeping large herds of domestic animals in the tropics has been made possible by the achievements of modern veterinary medicine, immunology, etc. The only difficulty to overcome is the question of providing sufficient feed for the animals.

The pods of the Theobroma fruits are available in many places. Heretofore they were considered disagreeable waste products. They were obtained by opening the fruits by means of cutlasses, machetes, and the like, removing the seeds or beans with the pulp from the pod husks by means of a spoon-like instrument, and subjecting the beans to fermentation. The relatively high potassium content of the remaining pods allowed their utilization as fertilizer to enrich the soil to a certain extent with said element. However, the rotting pods become very rapidly a dreaded source of infection with brown rot, black pod rot, and other microorganisms which grow very well on the slimy pods. Their use as fertilizer, therefore, was not recommendable. The native population in the tropics sometimes dried the pods, ashed them, and used the resulting ash as soap substitute in a similar manner as wood ashes were previously used for laundering.

It is well known that near the places where the cocoa fruits have been opened and the empty cocoa fruit pods were piled, withering and dying of all trees near that place are to be expected. Therefore, the marketing boards in the cocoa growing countries advise their farmers to burn or to burry these parts of the cocoa fruit. This advice, however, is usually not followed by the farmers as it causes additional work without any apparent financial reward.

The cocoa beans taken out of the parenchymatous tissue of the cocoa fruits with the smeary and juicy cocoa pulp attached thereto are submitted to the so-called fermentation process which differs traditionally in the various areas of cocoa tree cultivation. In West Africa, for instance, the beans are placed in heaps on large leaves, usually banana or plantain leaves, in amounts of 50 kg. to 500 kg. and the heaps are covered with banana or plantain leaves. In other areas the cocoa beans are fermented in holes in the ground or placed in baskets, wooden boxes, or empty barrels. Sometimes the places where fermentation takes place are of a size that can be called "central fermentation plants". For starting fermentation or for transporting the beans with the pulp to such fermentation plants, the farmers collect a sufficiently large quantity of cocoa beans with the smeary pulp attached thereto. In South America the beans and pulp are transported to the central fermentation plants in baskets attached to the sides of mules. Due to the time which elapses between the opening of the fruits and the start of proper fermentation, i.e. the moment when the temperature necessary to kill the germ of the cocoa beans starts to rise, the manner of storing the beans during the collection, the effect of the weather which causes drying out of the pulp or its liquefication, and other factors are responsible for the fermentation to start in a completely uncontrolled manner and sometimes not at all, differing from batch to batch and from day to day. Before the beans with the pulp reach the central fermentation plants many factors such as changes in temperature and duration of storage and transportation, humidity, the action of microorganisms, contamination and others, affect the fermentation so that it is quite impossible to carry out fermentation in an always uniform and controllable manner. This is the reason why, for instance, the farmers in Santo Domingo do not ferment their beans any more and, therefore, produce cocoa of varying and frequently inferior quality.

Up to now it was economically not feasible to transport the cocoa fruit as such, i.e. in the closed state to the fermentation plants because nine tenth of the weight of the cocoa fruit to be transported, namely the parenchymatous tissue thereof and the peels, simply had to be discarded as a waste product.

SUMMARY OF THE INVENTION

It is one object of the present invention to provide a novel and advantageous process of producing valuable products from all parts of the cocoa fruit in an economical and simple manner.

Another object of the present invention is to provide a novel and improved feed composition which is especially useful in feeding small animals such as rabbits, chicken, and the like, said feed composition being derived from cocoa fruits.

Still another object of the present invention is to provide a valuable texturising agent which is useful in the food industry but also for technical and industrial purposes.

Still another object of the present invention is to use the cocoa fruit tissue in its original state or partly, preferably up to 50% dried, as a whole or after separation of the cocoa fruit juice, so that the rougher or coarser part of the cocoa fruit tissue can be disposed of as a carrier substance for molasses.

Thus another object of the present invention is to provide molasses compositions containing as bodying agent the coarser part of the cocoa fruit tissue, said composition being of substantially solid consistency which permits to ship molasses in substantially dry form.

A further object of the present invention is to provide a nutritious animal feed composition of molasses and the cocoa fruit flesh or the coarser part of said cocoa fruit flesh which may be free of its cocoa fruit juice content.

Another object of the present invention is to provide a process of utilizing the pulp adhering to the beans by separating it, at least partly, therefrom by the action of microbiological agents, such as Saccharomyces, leuconostoc, or others.

Other objects of the present invention and advantageous features thereof will become apparent as the description proceeds.

It is a principal feature of the present invention to make use of the parenchymatous tissue of the cocoa fruit in its unaltered state, i.e. before it has become dry and/or lignified or woody and/or has been attacked by fungi and other microorganisms.

To achieve this result, the unopened cocoa fruits are treated in such a manner that no contamination of the cocoa bean pulp and/or of the cocoa fruit flesh can take place and that immediately after opening the cocoa fruits the separated cocoa beans and adhering pulp are submitted, without delay, to a controllable and well adjusted fermentation process.

The present invention contemplates two methods for separating the cocoa beans from the remainder of the cocoa fruit without contaminating the various useful components of the fruit. The first process has been claimed in the parent co-pending application Ser. No. 165,396.

The second process comprises the steps of treating unopened Theobroma fruits with a preserving agent for a period of time sufficient to neutralize any harmful substances on the surface of the fruit and stabilize lignification of the outer layer (peeling) of the fruit, thereafter drying the thus-treated fruits to a moisture content of less than about 70%, preferably between about 30% and about 60%, opening the dried fruits, removing and separating the cocoa beans therefrom. Almost any known preserving agent can be employed in this process, such as sorbic acid and salts thereof, sulfur dioxide, chlorine, chlorides, nitrates, hypochlorites, preferably those of the alkali metals, formaldehyde, disulfites, ozone, methylformate, diphenyl, sodium ortho-phenyl phenolate, nitrogen trichloride and others. Typically, the preserving agent is employed in the form of an aqueous solution of a low but effective concentration. The concentration of the preserving agent depends, of course, upon its effectiveness and varies considerably. Optimum concentrations which do not detrimentally affect the cocoa fruit, can readily be determined by a person skilled in the art by routine experimentation. It is also possible to apply the preserving agent by exposing the unopened Theobroma fruits to the vapors of vaporizable preserving agents, preferably diluted with air or inert gases. The treatment with the preserving agent varies also depending upon the concentration and effectiveness of the agent and may last for a period of time between about 1 hour and up to sixty days, preferably between 8 hours and 8 days although it is not limited to such a period of time.

The process described immediately above has been found extremely advantageous in connection with the production of an animal feed composition wherein the entire residue of the cocoa fruit, after removal of the cocoa beans with adhering pulp, may be utilized. After opening the dried fruits and removing and separating the cocoa beans therefrom, the residual fruit pods are then comminuted and intimately mixed with a relatively small quantity of a suitable edible fatty material, such as suet, lard, acidified soap stock, and vegetable oils. The size to which the pods are comminuted is of no particular significance but may reach the fineness of a puree which passes through an 0.005 inch screen of a paddle pulper. Depending upon the requirement and its subsequent use the pods may be comminuted so that they pass through an 0.05 inch to an 0.3 inch screen. Preferably its particle size is such that it passes through an 0.05 inch to an 0.12 inch screen. Such a particle size is required, for instance, when using the comminuted pods or fruit flesh as emulsifying agent in salad dressings and the like. A material of larger particle size is preferably used for converting molasses in a quasidry state, for instance, for making animal feed pellets of molasses and the cocoa fruit flesh.

Alternatively, the residual fruit pods may be comminuted to a fairly coarse size and then sieved to remove at least part of the crude fiber content before mixing it with the edible fatty material. The protein content of animal feed produced in accordance with the foregoing techniques can be increased by mixing the feed composition with protein precipitated from protein-containing waste waters of food processing plants, such as beef, hog, poultry, or fish processing plants. This may be achieved by either simply mixing the precipitated protein with the feed composition or by suspending the resulting feed composition in water, adding to the resulting suspension a protein-containing waste water which has been adjusted to the isoelectric point of the protein by the addition of acids whereby precipitation of a mixture of the fruit pods, fatty material, and protein takes place. This intimately mixed precipitation product can be separated and utilized as an animal feed.

Conventional grain variety animal feeds, for instance, sorghum, can be mixed with the cocoa fruit-derived feed composition in a ratio of from 1:1 to about 5:1 and preferably from about 2:5 to about 3:1.

It is, of course, also possible to admix to such feed compositions molasses and to produce pellets or other substantially dry feed compositions containing molasses.

Oil residues such as soybean meal, cotton seed residues, sesame seed residues and others, or fish meal may also be admixed to such feed compositions.

Cocoa fruits which have been treated in accordance with the first-mentioned process produce after opening the pods and removal of the cocoa beans and adhering pulp a residue which consists of only the parenchymatous or fruit flesh portion of the fruit. This may be compared to the edible portion of a honeydew melon after the peeling and seed-pulp mixture in the center of the fruit have been removed. When the fruits are processed in accordance with the present invention, this fruit flesh portion may be immediately rendered useful as an animal feed composition by comminuting it to an average particle size, preferably so as to pass through an 0.2 inch to 0.5 inch screen and drying the comminuted material until a dry, friable product is obtained.

Alternatively, the juice contained in the parenchymatous tissue of the cocoa fruit may first be expressed from the tissue and separated therefrom before the tissue is comminuted to the final desired size and dried to form a friable feed product.

The parenchymatous tissue of the cocoa fruit still containing the juice, or more importantly, the juice itself, comprises also a very useful additive for foods designed for human consumption, for cosmetic compositions, for detergent compositions and the like, as well as for other industrial compositions such as paints, printing paste, textile finishes and the like. When the parenchymatous tissue containing the juice is comminuted to an extremely small size, so as to form a material of paste-like consistency, it may be used directly as a texturizing agent for the various products mentioned above. An extremely valuable texturizing agent is achieved when the juice is separated from the tissue and purified, or more especially, when the juice is extracted to form the pure hydrocolloid derivative thereof. These texturizing agents act as thickening agents, extenders, and/or stabilizers for the ultimate products and can be employed in place of the conventional vegetable gum materials which have heretofore been used for this purpose. In food or beverage compositions, the texturizing agent is employed generally within the range of about 0.5% to about 75%, by weight, and preferably within the range of about 1% to about 5%, by weight. Particularly economical texturizing compositions are obtained by combining the cocoa fruit flesh texturizing agents with other conventional vegetable-derived texturizing agents in the ratio of from about 1:1 to about 1:2.

The pulp adhering to the beans can be separated therefrom, at least partly and the separated pulp is then subjected to the action of microorganisms to microbiologically transform the monosaccharides present therein. Not only microorganisms of the Saecharomyces type but also those of the Leuconostoc genus grow exceptionally well on the bean pulp as substrate.

DETAILED DESCRIPTION OF THE INVENTION

In accordance with the first process of the present invention for treating the cocoa fruits in order to completely utilize the various components thereof, the outer skin or peeling of harvested cocoa fruits is removed before the fruits are opened to remove the cocoa beans. Many varieties of cocoa fruits and especially younger fruits may have their peelings removed by simply subjecting them to various conventional techniques without first subjecting the fruits to any special treatment. However, an average mixture of harvested fruits contains a significant percentage of certain varieties and/or older fruits which require a pre-treatment before the peelings are removed.

For this purpose the cocoa fruits are treated with an alkaline bath such as an alkali metal hydroxide or, preferably, alkali metal carbonate bath at a temperature between about 50° C. and about 100° C. for a short period of time, e.g., generally from ½ minute to 30 minutes and preferably from 3 minutes to 8 minutes. Thereafter, the alkaline-treated fruits are passed through a heating zone, preferably through an infrared heated channel. The alkaline treatment at 50° C. to 100° C. for a short period of time causes the cocoa fruits to swell to a certain extent. This swelling facilitates subsequent removal of the outer layers of the fruits such as the peel. These outer layers are removed, for instance, by means of scrapers, knives, rollers, rubber discs, or the like means which rub off the peel. The preferred means of this type are rubber discs rotating at a high velocity, emery rollers, toothed or corrugated rubber or plastic rollers. It will be understood that lower temperatures and longer treatment times may also be employed.

After the outer peel has been removed in this manner, i.e., using an alkaline pre-treatment, the remaining fruit is neutralized and the action of enzymes on the fruit is reduced or completely eliminated by treating the fruits with a suitable acid, preferably an edible acid, such as citric acid, malic acid, tartaric acid, ascorbic acid, and the like edible acids. Phosphoric acid and hydrochloric acid may also be used. Treatment with sulfur dioxide is also possible and frequently of considerable advantage. The amount of acid added is such that the pH-value of the treated cocoa fruit is below a pH of 7.0 and preferably at a pH between about 5.0 and 6.0.

Removal of the peels before further treatment of the cocoa fruit flesh and the pulp is an essential feature of the present invention because thereby noxious and damaging microorganisms, herbicides, fungicides, insecticides, other agents sprayed thereon are also removed so that the parenchymatous tissue or fruit flesh can subsequently be utilized in a hygienic manner. Removal of the peels has the further advantage that the color of the resulting products is improved and no contamination of the final products by woody parts takes place.

After neutralization the neutralized or slightly acidified fruits are mechanically opened to remove the cocoa beans with the adhering pulp. Mechanical opening of the fruits is effected in suitable machines which do not cause damage to the beans, i.e., machines which effect bursting of the peeled fruits, for instance, by causing the peeled fruits to drop onto special devices by which they are passed through pressure rolls, crushers with jaws, conical drums, and the like apparatus capable of bursting the peeled fruits. Thereby the parenchymatous tissue or cocoa fruit flesh is separated from the cocoa beans with the adherent pulp by kind of a whirling treatment. For this purpose, the peeled cocoa fruits are placed, for instance, into an inclined rotating drum with perforated walls through which, preferably, a gas current, for instance, an air current or preferably an inert gas current is passed. The cocoa beans with the adhering pulp drop through the perforations while the fruit flesh remains in the rotating drum and is discharged therefrom, and the cocoa beans with the adhering pulp are immediately transported, while still warm, to the fermentation silos. Preferably they are placed on heated screw or worm conveyors. Or they are conveyed by means of a gas stream under pressure, such as compressed air of the required predetermined moisture content, and at the required temperature to the fermentation silos. While the cocoa beans with the pulp are conveyed in this manner to the silos, the necessary chemical, physical, enzymological, bacteriological, and other control tests are carried out at predetermined time intervals and, if required, necessary additives, such as carbohydrates, mixtures of mono- and disaccharides such as unrefined sugar juice or sugar solutions, acids, nutrients, yeast, trace elements, or compositions containing such additives are admixed to the beans so as to introduce into the fermentation silos agents which will ensure adequate and controlled fermentation.

According to the second embodiment of the present invention, the unopened, harvested cocoa fruits are placed directly into a bath or atmosphere containing a preservative, typically at a low but effective concentration of, for instance, between 0.2 and about 10%, and for a period of time sufficient to neutralize any toxic substances on the surface of the fruit and to stabilize lignification of the outer layer (peeling) of the fruit. To accomplish this generally requires between about 10 minutes and about 3 or more months of exposure to the bath or atmosphere depending upon the effectiveness and type of preservative used. Any known preservative can be employed in this step of the process, for example, sorbic acid, sorbic acid salts, sulfur dioxide, chlorides, nitrates, chlorine, hypochlorite, formaldehyde, disulfides, ozone, methylformate, diphenyl, ammonia, sodium o-phenyl phenolate, nitrogen trichloride, and others. The preferred preserving agents are sorbic acid, sulfur dioxide, chlorine, sodium chloride, hypochlorite, and formaldehyde, as many other known agents, although useful, tend to affect the taste and nutritive value of the treated pods.

After pre-treatment with the preservative, the pods are then dried to an extent that they contain less than about 75% moisture and, in some instances, less than about 30% moisture, depending upon their subsequent use. Drying may be accomplished in any conventional drying apparatus. The partly or fully dried fruits may then be opened either mechanically or by hand, for instance, by utilizing apparatus similar to that described above, and the cocoa beans may then be removed from the pods and subjected to further fermentation treatment as discussed hereinabove.

As indicated hereinabove, the portion of the cocoa fruit remaining after the cocoa beans have been removed, may be completely utilized to produce valuable food and additive products in accordance with the present invention, whereas heretofore this material has been considered as waste product. The parenchymatous or fruit flesh portion of the cocoa fruit may be used directly as it is produced as a by-product in either of the above-described treatment processes, i.e., either without the outer peel according to the first process or with the outer peel in accordance with the second process. Alternatively, the parenchymatous tissue may be pressed to remove the juice therefrom, whereupon the residual tissue as well as the juice which has been removed therefrom may be employed further as useful products.

The cocoa fruit flesh without the peels which has been separated from the beans and pulp adhering to the beans in accordance with the first process is passed into a disintegrator or a cutting machine and is further processed depending upon the purpose for which this material is to be used. Thus it may be subjected to the action of hydraulic presses, filter presses, centrifuges, steaming apparatus, mixing containers, pulpers, finishers, pasteurizers, sterilizers, roller mills, roll dryers, spray dryers, colloid mills, extruders and other suitable and required processing apparatus.

An especially valuable use of such cocoa fruit flesh, especially in the dried state, is the use as feed composition for animals. However, dried and ground cocoa fruit flesh as such, i.e., produced in accordance with prior methods of treating the cocoa fruit, cannot be used satisfactorily as feed for small animals such as rabbits and chickens. Since such animals are usually kept by the population in underdeveloped countries, especially in the tropics, there is a great need for supplying the farmer, especially in the tropical rain forest, with a valuable feed composition useful especially for small animals, which composition comprises the parenchymatous tissue of the cocoa fruit, i.e., its fruit flesh.

According to the present invention the parenchymatous tissue of the cocoa fruit obtained as described hereinabove after separating the peels, opening the fruits, and removing the flesh from the cocoa beans with the adhering pulp, is especially useful as feed for small animals. For this purpose, the resulting cocoa fruit flesh which is obtained in this process in large size pieces is comminuted so as to form small rod-like pieces of a width and a length of a few millimeters. Of course, the cocoa fruit flesh pieces can also be coarsely comminuted in any suitable type of disintegrator. The comminuted pieces may be used directly or they may be pressed out in a fruit juice press whereby a liquid juice is separated.

According to a specific embodiment of the present invention the comminuted small rod-like pieces are exposed to the action of steam. They can also be subjected to the action of preferably acid extraction agents such as hydrochloric acid, sulfuric acid, acetic acid, citric acid, and others.

Any of the known methods for the extraction and/or insolation of pectinic substances from plant material can be used for recovering the cocoa fruit flesh juice from cocoa pods, preferably from peeled pods. Especially useful has proved extraction of the cocoa fruit flesh with dilute acetic acid, preferably with 0.2 N acetic acid.

The residue remaining in the fruit juice press can be completely separated from the last amounts of residual liquid, for instance, by washing by means of brushing apparatus or by centrifuging. It is advisable to remove all slimy and gummy components from the resulting small cocoa fruit flesh pieces, because it is then possible to dry the residue to a friable material.

Tests with rabbits have shown that they accept readily such dried cocoa fruit flesh material as feed and that they show an increase in weight on prolonged feeding therewith.

The resulting cocoa fruit flesh material has also proved to be a satisfactory additive to chicken feed. In this manner the cocoa farmer is able to produce from cocoa fruit flesh a feed which can be used for feeding small domestic animals. Thereby use is made of a waste product, the elimination of which is rather difficult and, heretofore, could not be carried out without damaging the cocoa plantations.

Furthermore, the viscous liquid expressed from the cocoa fruit flesh as described hereinabove which amounts to more than 50% of the fruit flesh can be purified by chemical and physicochemical processes so that it is obtained in the form of a clear and transparent liquid which is odorless, colorless, and completely free of any solid impurities. Due to its valuable chemical and physical properties the cocoa fruit flesh juice can be used advantageously in the preparation of victuals. It can replace the known vegetable gums and has all the properties of such gums as they are desired by the consumer, producer, and salesman. The cocoa fruit flesh juice can be used, for instance, as additive to facilitate the manufacture of food products and to simplify their preparation, to eliminate the risks of faulty manufacture, and/or to render the manufacturing processes more economical.

The aid and additive obtained according to the present invention from cocoa fruit flesh juice is characterized by the following properties.

It has a surprisingly high stabilizing effect upon suspensions and emulsions.

It is capable of binding water.

It imparts a high viscosity to products to which it has been admixed and affects their texture favorably.

It preserves the aroma, odor, and/or color in products to which it has been added.

It improves the rheological properties of various substances and preparations. Thus the cocoa fruit flesh juice or the pectinic substances recovered therefrom have proved to be useful for the following purposes:

As bodying agent, thereby saving eggs, oil, mayonnaise, starch and completely or partly replacing other bodying agents such as vegetable gums, pectins, carboxy methyl cellulose, and the like.

As thickening and suspending additive to sauces, toppings, dippings, dressing, desserts, drinks, and the like.

As homogenizing and emulsifying agent, for instance, in beverages, wherein they homogenize and/or emulsify aromatic and coloring additives, sugar, and other additives in aqueous or alcoholic beverages.

As binding agent for binding solids, aromatic and coloring agents.

As extending agent for meat and vegetable proteins whereby they have a pronounced texturizing effect.

As viscosity increasing agent, for instance, in oil-water systems.

As stabilizing agent, for instance, for prolonging the shelf-life of products into which it has been incorporated.

As jellying agent, for instance, when added to sugar-containing solutions which, on heating for a short period of time and allowing the mixture to stand, forms a jelly block useful as jelly candy and the like.

The cocoa fruit flesh juice and/or the pectin-like product recovered therefrom is characterized by the following properties:

They can be frozen and thawed without any change in their usefulness and thus can be added to frozen dishes.

They can be diluted with water in any proportion.

They can be dried and redissolved.

Their properties are not substantially changed by cooking, baking, or frying.

They are ingredients of low caloric values but impart full mouthfeel to products into which they are incorporated.

They represent a natural fruit product.

Thus the cocoa fruit flesh juice or the pectinic product obtained according to the present invention can advantageously be incorporated into skimmed milk margarine, fruit juices, lemonades, fruit and vegetable puree, and others and can be used in the manufacture of beer, bakery and pastry products, mayonnaise, salad dressings, ketchup potato chips, alimentary pastes such as noodles and maccaroni, and others.

It can be added with great advantage to preparations to be spray-dried or roller-dried and has proved to be useful in the manufacture of aromatic preparations in powder form, for preserving the activity of vitamins, in the preparation of starch, sirups, gelled products, such as puddings, thickened soups and drinks, deep-frozen dishes, whipped and porridge-like products, such as potato puree, fish pastes, sausages, and in general in the preparation of all products which require a protective colloid, increased viscosity of the aqueous phase, and a thickening and stabilizing effect upon suspensions and emulsions, in preventing the drying out of pastes or creams due to loss of water, in retarding or preventing the formation of ice crystals, in the preservation of aroma and color, and for many other purposes.

A number of similar manufacturing aids and additives are known such as tragacanth, carboxymethyl cellulose, alginates, gum arabic, quince mucilage, carob bean flour, carageen, agar, pectins, modified starches, and the like. These additives are generally employed in food and beverages in an amount of about 20% to 80%, by weight, and preferably about 40% to about 60%, by weight. Heretofore the juice of cocoa fruit flesh in liquid and solid form has not been prepared and recovered from the cocoa pods, nor has its use for a similar purpose been suggested. In some instances the cocoa fruit flesh juice has advantages over the known vegetable gums and mucilages while in other instances it is at least equal to the known products. Furthermore, with some of them it produces synergistic effects when used together therewith.

Its use is advantageous not only for this reason but also because a noteworthy reduction in price is achieved when making use of the cocoa fruit flesh juice according to the present invention in combination with agar, carboxymethyl cellulose, gelatin, and other agents of this type. The ratio of cocoa fruit juice to other vegetable-derived compounds with which it is mixed is generally from about 1:4 to about 4:1 and preferably from about 1:2 to about 2:1. As stated above the cocoa fruit flesh juice according to this invention can be used in liquid form as well as in solid form, in the purified state or not completely purified, in concentrated or dilute solution, and in any other form as additive to food products or in the manufacture of food products to achieve the desired effect. Its main advantage over similar agents used for the same purpose is its cheapness. All the known manufacturing aids and additives of this type are produced as the main product in a separate operation. Or plants must be cultivated for producing such agents or must be collected. For instance, gum arabic must be collected; alginates must be recovered from maritime algae; agar likewise; pectin must be produced by complicated processes from apples or citrus fruit peels; carboxy methyl cellulose must be obtained by chemical reaction from wood or cellulose; starch must be obtained from carbohydrate-containing products, and gelatin from protein-containing products and the like. In contrast thereto the cocoa fruit flesh juice is obtained as a by-product in the production of cocoa beans and in working up the cocoa fruit flesh to feed preparations for small animals.

As stated above, the cocoa fruit flesh from which the juice has been obtained, has been considered heretofore as a valueless waste product the destruction of which was rather expensive and had a damaging effect upon the cocoa tree plantations. The process of the present invention now permits to recover a very inexpensive vegetable gum-like material from a waste product in large amounts since annually about 120 million tons of cocoa fruit flesh are accumulated in the world.

The cocoa fruit flesh and/or the cocoa fruit flesh juice is used in the tobacco industry as a binding agent in the manufacture of cigars and also of cut tobacco. For this purpose the cocoa fruit flesh, without separating or extracting the liquid part contained therein, is used as such or is dried and comminuted to a powder, and is very finely milled. Then the cocoa fruit flesh and/or the separated cocoa fruit flesh juice is homogenized and, if necessary, mixed with water to form a slurry of milk-like consistency, to which can be added small amounts of cellulose derivatives, e.g., carboxy methyl cellulose or oxidized cellulose, or small amounts of alginate derivatives and emollients such as glycerol or glycols, combustion modifiers such as potassium or sodium carbonates or sulfates, humectants, nicotine, tobacco aroma, coloring agents, flavoring agents, and casing material such as honey or alcohol.

Also tobacco which otherwise cannot be used, such as powder, dust, minced, and shredded pieces may be incorporated into the slurry. The composition of the slurry will be from 20% to 70% cocoa fruit flesh and/or from 8% to 30% of cocoa fruit flesh juice, 2% to 10% modified celluloses as carboxy methyl cellulose, up to 5% emollients, and the rest water. This slurry is spread as a very thin liquid film on an endless band which passes through a tunnel where the slurry film is heated so as to evaporate the water and form a solid sheet of the thickness, firmness, and consistency of thin silk-like paper or tobacco foils. This sheet may also pass over calanders and rollers where the above said ingredients may be applied on the pre-formed sheet instead of being incorporated into the slurry. The finished sheet may then be cut into flakes or shredded into small strips for use as smoking material.

As stated above, the cocoa fruit flesh juice is preferably used after purification. Such purification can be effected by filtration, gel filtration, suspending it with polyamides, ion exchange agents, or other purifying plastic materials and chemicals followed by allowing the treated juice to settle, by pasteurizing, sterilizing, centrifuging, freeze-drying, precipitating and re-dissolving, spray-drying, roller-drying and re-dissolving, reverse osmosis, electrophoresis, ion exchange reaction, and the like. Furthermore, the degree of viscosity of the resulting cocoa fruit flesh juice can be varied and adjusted as desired by concentrating the juice in a vacuum, by reverse osmosis, by changing its pH-value, by the addition of chemicals reacting therewith, and by any other suitable means.

The cocoa fruit flesh juice can be purified by ion exchange procedures. When percolating the juice through high molecular polymer gels such as polyamide resins, polymeric carbohydrate gels, dextrans, "Zeokarb" cation exchangers, and others in absorption columns in which, for instance, about one cu.m. of juice passes through 2 to 3 cu.m. of gel within one hour, there are retained by the gel the low molecular impurities such as bitter principles, dyestuffs, and the like while the viscosity building components pass first therethrough especially if different electric charges are applied to the opposed ends of the absorption column. It is also possible to purify the cocoa fruit flesh juice by intimately mixing it with absorbing agents, for instance, with activated charcoal, silica gel, high molecular polymers such as polyamide resins or polymer carbohydrate gels, and others, and filtering the mixture.

The high molecular polymer gels used in the absorption columns or for admixture to the juice are usually subjected before use to a pre-treatment with a suitable salt solution to cause it to swell and form the gel. Preferably the cocoa fruit flesh juice is pre-treated with such dilute salt solutions before the absorbing agent is added thereto.

The viscosity building agents can be recovered from the juice before or after the above described purification process, for instance, by precipitation with aluminum sulfate or copper sulfate, with 80% alcohol, or with mixtures of alcohol and acetone. The thus precipitated agents are washed and then again re-dissolved.

After purification in the described manner, the pH-value of the purified juice is adjusted to the optimum pH-value for its desired use.

Preferably the cocoa fruit flesh juice is separated from the cocoa fruit flesh by expressing, centrifuging, or extracting. It is a slimy, viscous liquid which is recovered from cocoa fruits which have been subjected — before further processing — to the hereinabove described pre-treatment to completely separate therefrom any residual lignified components which are formed due to aging of the parenchymatous tissue. Removal of such lignified components is effected, for instance, by a treatment of the cocoa fruits with alkaline solutions or with methylene chloride or other suitable organic chlorine-containing solvents at suitable temperatures. Thereafter, the fruits are freed from such components by means of scrapers, rollers, discs, brushes, knives, emery paper, or other means. Under certain especially favorable conditions, the cocoa fruit flesh juice can be recovered from the fruit flesh without such a pretreatment.

As stated above, in purifying the cocoa fruit flesh juice which is expressed from the parenchymatous tissue, the known procedures for recovering pectinic substances from materials containing same are employed. Especially advantageous has proved the method of extracting the cocoa fruit flesh or the dried fruit flesh juice with dilute acids, preferably dilute acetic acid solutions, preferably at an elevated temperature. The extracts are then mixed with an alcohol, preferably ethanol, whereby the hydrocolloid present in the cocoa fruit flesh or its juice precipitates. Other conventional methods of isolating pectinic substances can, of course, also be used.

The cocoa fruit flesh juice after separation from the parenchymatous tissue or after concentration can be sterilized, preferably by heating it between heating plates to about 98° C. for a short period of time, for instance, for 2 minutes, rapidly cooling it, and filling and sealing it in cans. The juice can then be stored for a prolonged period of time.

In a preferred embodiment of the present invention, the juice removed from the parenchymatous tissue is treated further to derive therefrom the dry hydrocolloid derivative of the juice.

The isolated hydrocolloid is composed of galacturonic acid, galactose, rhamnose, arabinose, and xylose as determined by paper chromatography of the acid hydrolysate with the galacturonic acid forming the major part of its carbohydrate content.

As with the juice itself, the hydrocolloid derived from the juice may advantageously be blended with other vegetable hydrocolloids which are conventionally employed in the various utilities set forth above. Examples of some of the more common and more preferred vegetable hydrocolloids per agar, carboxy methyl cellulose, gelatin, and others. Typically, the present hydrocolloid may be admixed with the conventional vegetable hydrocolloids in a ratio of about 1:100 to about 1:1 and preferably of about 1:100 to about 1:10, although any other amounts of the fruit flesh juice or its hydrocolloid can be admixed to the known hydrocolloids.

According to another embodiment of the present invention wherein the unopened cocoa fruits are placed into a bath containing a preservative and are dried after such a preserving pre-treatment while still in the unopened state, and then the partly or fully dried fruits are opened and the seeds removed, a feed composition may be obtained by a process wherein the dried pods are ground and are passed through a roller mill or the like together with a suitable fatty material. When proceeding in this manner the advantage is achieved that a larger portion of the fruit flesh is dried and is incorporated with its valuable components into the feed compositions.

The amount of fatty material added is calculated so that about 2% to 4% thereof is contained in the final feed composition. Various fatty materials can be used for admixture with the ground pods, such as suet, lard, acidified soapstock, vegetable oils, and others. The fatty material should be well stabilized, should be of low water content, and should have a low content of unsaponifiable matter.

The fat containing ground pods or the pure, dried parenchymatous tissue which represent the feed compositions according to the present invention may be mixed with other conventional grain variety feeds, such as copra meal, rice bran, sorghum, wheat bran or with oilseed residues such as soy meal, cotton seed meal, and others. Typically, from 10% to 50% of the final feed composition, but not limited thereto, can be comprised of such conventional grains and/or oil seed residues and feed nutrients. Also, mineral salts and/or other additives may be incorporated in conventional amounts. Such mixtures are more readily accepted and much better utilized by and thus much better compatible to cattle than the feed composition without such admixtures.

The ground Theobroma pods produced and prepared as described according to the second embodiment hereinabove can also be used as chicken feed, preferably after they have been pelletized. For this purpose it is of advantage to grind the Theobroma pods not too finely, for instance, to a particle size of between 0.1 mm. and 100 mm. and preferably between 2 mm. and 8 mm. and to remove therefrom as much of its crude fiber content as possible by sieving the ground pods before the fat is added.

For certain feeding uses the protein content of the feed compositions according to the present invention may be substantially increased by suspending the Theobroma pod meal in water and adding thereto waste waters of food processing plants such as fish processing plants, dairies, slaughter houses, and the like which contain in dissolved form, proteins, proteides, such as nucleoproteides, nucleic acids, polysaccharides mainly composed of amino sugars, and others.

The protein and other high molecular substances with basic groups may be precipitated from these waste water solutions by known protein precipitation methods, for instance, by adjusting the pH-value to the optimum value required to cause precipitation. Adjustment of the pH-value by the addition of a mineral acid to a pH of 5.0 and lower has proved to be useful for this purpose.

Alternatively, the protein-containing waste water can be added to a suspension of the ground pods and a final feed composition precipitated. In this case, the waste waters are adjusted to the isoelectric point of the protein contained therein before they are added to the Theobroma pod suspension, for instance, by the addition of acids such as phosphoric acid, hydrochloric acid, acetic acid and others. Addition of the Theobroma pod suspension causes more rapid settling of the coagulated protein. Thereby the further advantage is achieved that the waste water protein is well mixed with the settling Theobroma pod meal because the high pectin content of the latter has an especially favorable effect upon protein precipitation. The resulting precipitate is separated from the liquid, for instance, by flotation and is then dried. It represents a highly valuable, protein-rich, nutritious feed or additive to feedstuffs.

When adding this protein supplemental to the feed composition produced in accordance with the present invention, there is typically combined approximately between 10 l. and 50 l. of protein-containing waste water per hundred kg. of ground cocoa fruit pods, or the equivalent amount of pre-precipitated protein from this amount of waste water.

As stated above, the ground Theobroma fruit pods or fruit flesh and preferably the fruit flesh from peeled Theobroma fruits have proved to be useful for converting molasses into a form of substantially solid consistency so that it can be shipped in substantially dry form. Mixtures of such pods or the fruit flesh or the coarser parts of said fruit flesh which may or may not contain the cocoa fruit flesh juice, with molasses and, if desired, with other feed additives such as oil seed residues, grain variety feeds, the proteinic components of waste waters of slaughter houses, dairies, fish processing plants, and the like yield highly nutritious animal feed compositions and allow to utilize molasses in substantially dry form. The amounts of Theobroma fruit pods or fruit flesh to be added varies considerably depending upon the amount of molasses as well as the amounts and kinds of the other components added.

DESCRIPTION OF THE PREFERRED EMBODIMENTS

The following example serve to illustrate the present invention without, however, limiting the same thereto.

EXAMPLE 1

55 kg. of cocoa fruits are placed into a 30% potassium carbonate solution heated to a temperature of 70°–75° C., said solution containing a wetting agent. The cocoa fruits are stirred in said solution for about 10 minutes. They are then passed through an infrared heating channel to an aggregate of brushes and of toothed rubber disc rollers rotating at a high velocity. Said aggregate causes rubbing off of the peels. Thereafter the peeled fruits are showered and dipped into a bath containing 10% citric acid and 5 g./liter of sulfur dioxide. As soon as the peeled fruits are neutralized, they are placed between the jaws of a squeezing device and are then passed through rotating rollers causing bursting and breaking open of the fruits to expose the beans with the pulp adhering thereto. The opened fruits are then introduced into rotating wire net drums, preferably plastic net drums, wherein the beans with their adhering smeary pulp coating are separated from the parenchymatous tissue and drop through the perforations onto a heated screw or worm conveyor while the parenchymatous tissue remains in the rotating wire or plastic net drum. Preferably the beans with adhering pulp are freed from small amounts of contaminating cocoa bean flesh by means of vibrating screens arranged before the screw conveyors. In this manner about 10 kg. of cocoa beans with adhering pulp and 45 kg. of cocoa fruit flesh are obtained. The beans are mixed with suitable additives to insure proper and satisfactory fermentation. Such additives are, for instance, molasses which have been enriched by the addition of yeast, yeast enzymes, or the like fermentation additives and aids. In place of molasses there can also be used crude sugar juice containing mixtures of mono- and disaccharides recovered from plants of the grass family. Fermentation is then carried out in the conventional manner.

In place of potassium carbonate solution, there can also be used sodium hydroxide solution preferably of a concentration between 15% and 30%. The duration of the alkaline treatment is dependent upon the temperature at which it is carried out and the concentration of the alkaline agent. The higher the temperature and/or the higher the concentration of the alkaline agent, the shorter the duration of the alkaline treatment.

In place of 10% citric acid as used for washing and neutralizing the peeled cocoa fruits, there can be used other acids as mentioned hereinabove in a concentration from between 2% and about 50%. Preferably sulfur dioxide in an amount between about 2 g./liter to about 10 g./liter is added to said solution.

EXAMPLE 2

The cocoa fruit flesh obtained according to the preceding example is used as food for small animals. Rabbits received a mixture of 75% of cocoa fruit flesh obtained according to the present invention and 25% of barley for 10 days. The weight of the animals remained unchanged and amounted to 3,280 kg. per rabbit.

Thereafter the rabbits received a feed consisting of 100% of cocoa fruit flesh according to the present invention for 30 days. During the first 4 days the weight of the rabbits decreased to 2.800 kg. per rabbit but started to increase thereafter and amounted to 2.975 kg. per rabbit after 7 days, to 2.950 kg. per rabbit after 10 days, and to 2.970 kg. per rabbit after 30 days. When feeding thereafter the rabbits a mixture of 80% of cocoa fruit flesh produced according to the present invention and 20% of barley, the weight of the rabbits increased after feeding for 3 days to an average weight of 3.045 kg. per rabbit. The loss in weight during the first days after changing the feed to a feed composition solely consisting of cocoa fruit flesh is due to the fact that the animals must become adjusted to the new feed.

As an average the cocoa fruit flesh is composed as follows:
8% of water
9.2% of crude ash
0.7% of crude fat
5.1% of crude protein
40.0% of crude fiber
36.3% of nitrogen-free extractive agents
1.50 g./kg. of total phosphorus content
2.4 g./kg. of total phosphoric acid content
12.8 g./kg. of invert sugar
5.9 g./kg. of calcium
2.1 g./kg. of magnesium
17.7 g./kg. of sodium (determined by flame photometer)
11.2 g./kg. of potassium
34.1 mg./kg. of carotene
260 mg./kg. of vitamin C
1.31 mg./kg. of vitamin $B_1$
2.63 mg./kg. of vitamin $B_2$.
1000 g. of cocoa fruit flesh yield about 1785 calories.

The average amino acid content of the dried cocoa fruit flesh is as follows:

| | |
|---|---|
| Lysine | 0.30% |
| Threonine | 0.11% |
| Valine | 0.16% |
| Methionine | 0.29% |
| Isoleucine | 0.15% |
| Leucine | 0.29% |
| Tyrosine | 0.05% |
| Phenyl alanine | 0.19% |
| Tryptophan | 0.02% |
| Histidine | 0.04% |
| Ammonia | 0.02% |
| Arginine | 0.01% |
| Aspartic acid | 0.30% |
| Glutamic acid | 0.40% |
| Serine | 0.32% |
| Proline | 0.08% |
| Glycine | 0.18% |
| Alanine | 0.18% |
| Cysteine | 0.06% |
| | 3.15% |

It is evident that all essential amino acids are present in the cocoa fruit flesh.

The feed preparation according to the present invention has also proved of value as admixture to chicken or generally poultry feed. Thus, the cocoa farmer is enabled by the present invention to produce a valuable feed material for his domestic animals from cocoa fruit flesh, i.e. from a waste material which heretofore could be eliminated with difficulty only.

The following examples serve to illustrate the use of cocoa fruit flesh juice as prepared according to the present invention for various purposes.

EXAMPLE 3

The cocoa fruit flesh residue obtained after separating the cocoa beans with adhering pulp as obtained according to Example 1 hereinabove, is placed into a curb press, as it is conventionally used in the production of cider or other fruit and vegetable juices, wherein it is enclosed in a cylinder, for instance, of perforated steel plate and is compressed by a solid ram. The fruit flesh juice escapes thereby through the walls of the cylinder and flows to collecting channels. The collected fruit juice is used either as such or after further purification and, if desired, concentration as plant hydrocolloid material in Examples 4 to 37 given hereinafter while the expressed cocoa fruit flesh is used as animal feed as described in Example 2 hereinabove.

Other presses such as they are known to the art, for instance, box presses, pot presses, cage presses, or continuous screw presses can, of course, also be used.

Instead of expressing the cocoa fruit flesh obtained from peeled cocoa fruits according to Example 1, it is also possible to express the cocoa fruit flesh which still contains the peels by first treating the unopened cocoa fruits with a preserving agent, opening them, removing the beans and adhering pulp, and grinding the remaining peels and fruit flesh.

It is, of course, also possible to use the expressed fruit flesh which still contains the peels as feed composition as described in Example 2 hereinabove, preferably after drying and comminuting the same. The results achieved by feeding such a feed material to rabbits are about the same as those achieved by feeding the material of Example 2, i.e., expressed cocoa fruit flesh without the peels.

EXAMPLE 4

To each cu. m. of cocoa fruit flesh juice obtained according to Example 3 by pressing the cocoa fruit flesh, to which 0.002% of sodium azide have been added to protect it against decomposition by microorganisms, there are added 100 cc. of a 10% sodium chloride solution. The mixture is then passed through a column which is filled with about 3 cu.m. of a high molecular polymeric carbohydrate gel that as been caused to swell by a pre-treatment with the same salt solution. The percolation speed is adjusted so that about 2 cu.m. of the cocoa fruit flesh juice pass through the column hourly. The purified juice is substantially free of bitter components and coloring matter and can be used for many purposes as described in the following examples.

EXAMPLE 5

Production of Buttermilk Margarine

The cocoa fruit flesh juice is dissolved preferably in buttermilk and is then added to the margin mixture composed of an edible oil, such as cotton seed oil, buttermilk, and salt. Preferably, the cocoa fruit flesh juice is of high viscosity. A margarine mixture is, for instance, composed as follows:
1.25% of cocoa fruit flesh juice
80% of cotton seed oil
15.15% of buttermilk
3.0% of salt
0.6% of sodium benzoate.

The margarine production is carried out in a manner known per se.

The addition of cocoa fruit flesh juice serves as emulsifier and as stabilizer in place of lecithine, egg yolk, or other emulsifiers as conventionally used in margarine manufacture.

EXAMPLE 6

Paste-like Fruit Essence 30 g. of comminuted dried oranges are stirred into 300 g. of water and are then mixed with 80 cc. of almond essence. 350 g. of cocoa fruit flesh juice of a viscosity of 3,000 Cps. are admixed thereto. The resulting paste-like fruit essence preparation is filled in the tubes.

In place of dried oranges, there may be used any other fruit to produce the desired fruit essence in paste form.

EXAMPLE 7

Preparation of Dry Potato Chips of Golden Yellow Color for Deep Freezing and Subsequent Use The raw potato chips are subjected to a blanching process at 85°–90° C. for about 5 minutes whereby the potato chips are partly boiled, the enzymes are inactivated, and part of the natural sugar components are removed. The chips are then dipped into a sugar-containing solution to compensate for the loss of the sugar dissolved therefrom in the blanching process. Said sugar-containing solution has admixed thereto cocoa fruit flesh juice to impart thereto a viscosity of 100 Cps. The temperature of said sugar containing solution is about 65° C. Thereafter, the sugar impregnated chips are fried in fat at 190° C. for one minute, the fat is allowed to drip off, the chips are packed, deep frozen, and stored. For subsequent use they are fried directly from their deep-frozen condition. They are distinguished over other potato chips by their light yellow color.

EXAMPLE 8

Brown Sauce, Stable on Boiling, as Additive to Meat Dishes

The sauce is composed of
40.5% of cocoa fruit flesh juice which may still contain some solid matter,
44.9% of water,
3.8% of skimmed milk powder, 0.8% of salt,
0.3% of sugar,
7.0% of margarine,
0.3% of meat extract sold under the trademark "MAGGI FONDOR",
0.2% of meat extract,
0.2% of onion aroma, and
2.0% of caramel.

The cocoa fruit flesh juice is heated to about 90° C. The skimmed milk powder is slowly stirred thereinto. Sugar, salt, molten margarine, "MAGGI FONDOR", meat extract, and caramel are slowly incorporated into the mixture while stirring. The viscosity of the resulting sauce can be adjusted by slowly adding the desired amount of water thereto. Preferably the resulting mixture is passed through a colloid mill to homogenize the same and is finally packed into plastic bags and rapidly deep-frozen. It can be stored indefinitely. On defrosting and heating, a gravy is obtained which can be boiled repeatedly, if required, without losing its consistency.

The sauce can also be prepared, especially when it is to be added to vegetables, with soybean protein or whey powder which partly replace the skimmed milk powder.

The cocoa fruit flesh juice can be added to any liquid or fluid material to be applied, sprayed, or coated on any kind of surface. It can also be used in any dipping and the like process. It imparts to such a liquid or fluid increased viscosity so as to improve the properties of the products to which it is added. Any aqueous system benefits from the improved flow characteristics caused by the addition of cocoa fruit flesh juice. For instance, the combination of sugar, syrups, whether made from corn starch or by boiling sugar solutions, with cocoa fruit flesh juice produces considerable advantages on subsequent use of such sugar syrups.

The resulting syrup differs from a syrup to which no cocoa fruit flesh juice has been added, by not having the objectionable very sweet taste of sugar syrup although its viscosity is the same, and by providing an excellent mouth feel or taste sensation in the mouth from the food to which the syrup has been applied. It was found that one third of the amount of starch in such sugar syrups can be replaced by the cocoa fruit flesh juice. As a result thereof the starchy taste of premature gelling effect of the starch is considerably reduced while the viscosity of the resulting starch product is increased.

The cocoa fruit flesh juice has proved to be useful as a stabilizing, emulsifying, suspending, and bodying agent. The viscosity of its aqueous solution is not affected by changes in temperature so that solutions prepared in the cold and used at increased temperature have essentially the same unchanged viscosity. Thus products marketed under different climatic conditions are free of changes in their consistency. The viscosity of cocoa fruit flesh juice is also not substantially changed when varying the pH-value of its solutions.

The vegetable hydrocolloid derived from cocoa fruit flesh juice differs from the known vegetable gums such as
(a) exudates or saps of trees, for instance, karaya gum, tragacanth, gum arabic;
(b) extracts from seeds, for instance, locust bean gum, guar gum, quince seed gum;
(c) extracts from seaweeds, for instance, agar, Irish moss, Kelp;
by its preparation; for it is expressed from the parenchymatous tissue of the cocoa fruit. Of course, it is also possible to extract the vegetable hydrocolloid from cocoa fruit flesh juice by suitable extracting agents, such as acids, especially, acetic acid.

EXAMPLE 9

Salad Dressing, Dippings, or Bread Spreads of the Russian Dressing Type

This preparation is composed as follows:
Vinegar: 12%
Water: 6.7%
Solid egg yolk: 1.5%
Sesame oil: 53.2%
Cocoa fruit flesh juice in powder form: 0.3%
Salt: 2.1%
Sugar: 12.0%
The remainder consists of spices such as onion powder, mustard powder, and garlic powder.

EXAMPLE 10

Salad Dressing, Dippings, Bread Spreads of the French Dressing Type

This dressing is composed as follows:

Water: 31.5%
Cocoa fruit flesh juice in powder form: 0.9%
Sugar: 16.5%
Salt: 1.2%
Sesame oil: 34.3%

EXAMPLE 11

The cocoa fruit flesh juice is used in the tobacco industry as a binding agent in the manufacture of cigars and cut tobacco. For instance, 0.5 kg. to 3 kg. of broken and defective tobacco shreds and tobacco dust are finely ground and moistened with from 4 liters to 7 liters of water to form a slurry. To the slurry are added 1 liter to 2 liters of cocoa fruit juice and 3 kg. to 5 kg. of finely comminuted cocoa fruit flesh. The resulting slurry contains between about 16% and 20% of solid material. This renders the slurry capable of being spread upon a conveyor belt without being too thin so as to run over the sides of the conveyor. The conveyor carrying the slurry then passes through a tunnel where it is heated to effect complete drying and is then cooled, whereby the slurry is transformed into a continuous dry sheet. The average weight of the dry sheet is between 50 g. and 250 g. per square meter.

Alternatively, the foregoing slurry may contain between 3% and 10% of an agent to modify the burning rate, for instance, hydrolyzed alumina, magnesium citrate, potassium carbonate, or the like. The slurry may also contain flavoring agents, approximately 2% to 3% of a cellulose derivative, preferably carboxy methyl cellulose, small amounts of nicotine, small amounts of ammonium compounds to regulate the pH-value of the product, and emetics or the like. However, a slurry based solely upon the cocoa fruit flesh and the juice derived therefrom produces an acceptable, smokable product.

EXAMPLE 12

Smokable Fleece as Tobacco Leave Substitute

The cocoa fruit flesh juice is converted into a fine paste and is mixed with water, a cellulose derivative or alginate, glycerol or glycol, tobacco dust, and coffee dust to form a slurry which consists of
20% to 50% of cocoa fruit flesh juice,
2% to 10% of a cellulose derivative or alginate, preferably carboxy methyl cellulose,
less than 5% of a softening agent, i.e., glycol or glycerol,
up to 1% of an agent modifying burning such as potassium or sodium sulfate or carbonate,
a small amount of the desired aromatic additive, and if desired,
honey or coffee ground.
The mixture is made up with water to yield 100% and is then passed on a conveyor belt through a heating tunnel as described in Example 11. A solid fleece of the thickness, consistency, and tearing strength of tobacco leaves is obtained which is further processed in a similar manner as said leaves.

EXAMPLE 13

The cocoa fruit flech juice is added in an amount of 5% to 10% to conventional dish washing liquids. It improves the detergency of such liquids and reduces redeposition of food soil on the dishes or glassware washed therewith.

EXAMPLE 14

The cocoa fruit flesh juice is incorporated in amounts up to 20% in gluten-poor flours of corn starch, wheat starch, or cassava starch. On baking, a crust similar to that of the crust of rye bread or wheat bread is produced from such a flour. The addition of cocoa fruit flesh juice has the further effect that the crust retains its freshness for a prolonged period of time and that the bread made from such starch flour has a better chewability or masticability than bread made from starch flour without the addition of cocoa fruit flesh juice. The dough is prepared in the conventional manner with the addition of baking powder or yeast.

EXAMPLE 15

Cocoa fruit flesh juice added to flour and intimately mixed therewith produces baked goods similar to omelettes. It replaces the eggs partly or completely therein. For preparing such omelettes, the cocoa fruit flesh juice mixture with flour is poured into hot oil in a frying pan and is then baked.

For this purpose, for instance, 500 g. of cassava starch are beaten very thoroughly with 100 g. of water and 200 g. of cocoa fruit flesh juice with the addition of 75 g. of yeast, 50 g. of sugar, and 1.5 g. of salt. The yeast may be replaced by baking powder in an amount yielding about the same amount of carbon dioxide as yeast on heating. The resulting dough is put into a greased baking mold and is baked in a baking oven.

EXAMPLE 16

The cocoa fruit flesh juice is added as creaming and thickening agent to rubber latex. Amounts of 0.2% to 0.5% by weight, calculated for the rubber concentrate solids, are added thereto and cause the natural rubber latex to separate into a layer containing more than 55% of rubber, within 24 hours.

EXAMPLE 17

Cocoa fruit flesh juice can also be used to produce a milk substitute useful as coffee whitener. Such a milk substitute is composed as follows:

Mixture of sodium caseinate and soybean caseinate: 3.0%
Lecithin: 0.8%
Sodium dihydrophosphate: 0.1%
Corn sirup: 7.5%
Cocoa fruit flesh juice: 2.0%
Sucrose: 7.5%
Water: up to 100%.

EXAMPLE 18

A hair shampoo is obtained by mxing coconut oil with potassium carbonate and adding cocoa fruit flesh juice thereto in amount of 4%.

EXAMPLE 19

Glass Cleaning Detergent

It is composed of a mixture of
Sodium hydroxide in flakes: 85%
Hexasodium metaphosphate: 10%
Triethanolamine: 3%
Cocoa fruit flesh juice: 2%
The resulting mixture represents a freely flowing detergent material.

EXAMPLE 20

Toilet Soap with a Low Fatty Acid Content

The cocoa fruit flesh juice serves as plasticizer in toilet soaps with a low fatty acid content of not more than 5%.

EXAMPLE 21

A cleaning composition is composed as follows:

Bentonite: 60 kg.
Clay: 30 kg.
Kaolin: 30 kg.
Water: 12 kg.
Cocoa fruit flesh juice: 14 kg.
Sodium silicate: 1.5 kg.
Sodium carbonate: 0.6 kg.
Perfume: 1.5 kg.

EXAMPLE 22

Hair Decurling or Straightening Liquid

The liquid contains between 2% and 16%, by weight, of sodium sulfate,
between 1% and 12%, by weight, of thioglycolic acid or the triethanolamine salt of said acid, and
between 1% and 15%, by weight, of cocoa fruit flesh juice as fixing agent.

EXAMPLE 23

Shaving Soap 60 parts of soap
20 parts of cocoa fruit flesh juice, and
20 parts of talcum
are intimately mixed with each other. Preferably a potassium soap is used to yield a paste which can be shaped.

EXAMPLE 24

Fat-free Sunscreen Ointment

75 Parts of water are intimately stirred with 5 parts of purified viscous cocoa fruit flesh juice, 5 parts of sorbitol sirup, and 3 parts of $\beta$-methyl umbelliferone with the addition of triethanolamine acetate to form an ointment.

EXAMPLE 25

4 Parts of cocoa fruit flesh juice are slightly heated with 2 parts of rose water. 5 Parts of sorbitol sirup and 20 parts of glycerol are intimately admixed thereto to yield a gel-like hand lotion. Perfumes and preserving agents are finally added thereto. Preferably boric acid is used as preserving agent. Before addition, it is heated with glycerol to about 90° C.

EXAMPLE 26

A so-called American lotion which represents an emulsified, highly viscous composition, is produced by first dissolving 6 parts of glycerol in 38 parts of water with the addition of 0.3 parts of triethanolamine. To the resulting solution there is added, while stirring vigorously, a 72° C. hot fatty melt consisting of 1.2 parts of stearin, 0.3 parts of ricinoleic acid, 0.3 parts of glycerol monostearate, and 0.3 parts of almond oil. The resulting mixture is cooled to 55° C. Thereafter, 50 parts of purified cocoa fruit flesh juice are admixed thereto while stirring. The resulting composition is allowed to stand for 24 hours, whereafter a perfume and a preserving agent are added thereto. The resulting creamy composition is homogenized by passing it through a sieve and/or, if required, through a colloid mill.

EXAMPLE 27

Printing Paste

A conventional printing paste can be thickened by the addition of cocoa fruit flesh juice. The printing paste can be used not only for machine printing, but also for silk batik screen printing, and in other textile printing operations. The cocoa fruit flesh juice-containing printing paste gives sharp, not bleeding lines and contours. No plugging of the screeen is encountered. The flow properties of the printing paste can be varied by the addition of a polyphosphate. After printing, residual printing paste can be removed easily by means of water. The cocoa fruit flesh juice is added to the printing paste in an amount between about 3% and about 10%.

EXAMPLE 28

Use of Cocoa Fruit Flesh juice in Spinning and weaving

Resistance against friction of the threads in textile fabrics, staple fiber, cotton fabric, and spun silk is considerably increased by using corn starch mixed with cocoa fruit flesh juice as finishing preparation.

EXAMPLE 29

Cocoa fruit flesh juice can be added to paints based on siccative oils or drying oils, i.e. water colors in combination with such oils. The oil content is between about 5% and about 10%. A suitable paint is composed, for instance, as follows:
Titanium dioxide: 52 kg.
Glue: 6 kg.
Cocoa fruit flesh juice: 3 kg.
Water: 24 liters
Phenolate: 100 g.
Sodium hexametaphosphate: 150 g.
Drying oil: 6.5 kg.
The paint is prepared by dissolving glue and the cocoa fruit flesh juice in water. Sodium hexametaphosphate and the preservative are added thereto. The pigment is boiled with part of the resulting solution. The oil is emulsified with the remainder of said solution. Thereafter, both parts are combined.

EXAMPLE 30

Waterproof paper is obtained by impregnating paper with a solution of
30 kg. of neutralized glue,
6 kg. of glycerol,
2 kg. of a highly viscous cocoa fruit flesh juice and
58 kg. of water.
The impregnated paper is then dried.

EXAMPLE 31

Bread spread or salad dipping 495 g. of an edible oil are intimately mixed with a mixture of 10 g. of onion powder, 5 g. of garlic powder, 10 g. of mustard, 310 g. of cocoa fruit flesh juice rich in solid matter, 100 g. of vinegar, 100 g. of invert sugar, 30 g. of salt, and 40 g. of whey powder. Water is added to said mixture in an amount sufficient to impart to the mixture the consistency required for use as a bread spread or as a salad dipping. 0.05% of a preservative such a p-benzoic acid, sorbic acid, potassium sorbate, or the like may be added to the composition.

EXAMPLE 32

Milk Ice Cream 15 kg. of refined sugar,
1.5 kg. of dried egg powder,
20.6 kg. of condensed skimmed milk (30%), and
8 kg. of cocoa fruit flesh juice
are intimately mixed with
35 kg. of milk
and are cooled below the freezing point to produce the ice cream. If desired, the mixture may be pasteurized for a short period of time before freezing. In place of the cocoa fruit flesh juice there may be used 400 g. of a dry powder obtained by drying the juice. In this case the amount of milk added is increased to 42 kg.

EXAMPLE 33

Milk containing chocolate beverage

A milk containing chocolate beverage which remains in uniform suspension for a prolonged period of time is obtained by intimately mixing at 70° C. 325 liters of milk with 2% of butter fat or an aqueous preparation of a corresponding amount of milk powder with 4 kg. of dried cocoa fruit flesh juice or 30 liters of thinly liquid cocoa fruit flesh juice, 320 g. of the dried component of Iceland moss, 8 kg. of trisodium phosphate, and 40 kg. of cocoa powder. The cocoa fruit flesh juice may be replaced by 100 liters of clear, purified cocoa fruit flesh juice and the dried cocoa fruit flesh juice powder may be obtained by adding to the juice modified starch before drying.

EXAMPLE 34

Spreadable Cheese 26.5 kg. of chester cheese with a fat content of 50% and corresponding to 16 kg. of dry substance and 11.0 kg. of another kind of cheese with a fat content of 20% and corresponding to 5 kg. of dry substance are mixed in a caldron with 1.95 kg. of sodium citrate and between 0.15 kg. and 0.25 kg. of dried cocoa fruit flesh juice. 18 kg. to 22 kg. of water depending upon the desired dry content of the final cheese product are admixed thereto. The mixture is stirred at 74–76° C. for about 3 minutes. After standing for 3 more minutes, the resulting spreadable cheese, while still warm, is filled into containers for sale.

In place of the dried cocoa fruit flesh juice, there can also be used the liquid juice whereby the water addition is reduced according to the water content of the juice.

EXAMPLE 35

Pie Filling 100 g. of cocoa fruit flesh juice which is rich in solid matter are mixed with 30 g. of apple sauce or 30 g. of pumpkin puree are mixed with each other. 20 g. of sugar and 20 g. of invert sirup and 10 g. to 30 g. of modified starch, depending upon the desired firmness of the final product, are admixed to said mixture and the resulting filling is aromatized by the ddition of cinnamon. A usual pie dough is spread out in an aluminum baking pan to cover its bottom and side walls. The above described pie filling is then filled into the pan to a height of about one inch and the cake is baked at a temperature between 185° C. and 200° C. Thereby, a readily sliceable fruit cake-like pie is obtained.

EXAMPLE 36

Refreshing Beverage 900 g. of cocoa fruit flesh juice which is rich in solid matter is intimately mixed, while stirring, with such an amount of invert sugar that the dry substance content of the mixture is about 30%. The mixture is thoroughly homogenized while vitamin C, citric acid, and the desired fruit aroma are added. To render the resulting beverage stable for a prolonged period of time, it is sterilized preferably by short time pasteurization at 90° C. The beverage can be diluted with water and/or carbon dioxide can be added thereto.

EXAMPLE 37

Meringue-like Dessert

The eggwhite of five eggs is mixed with half of its weight of cocoa fruit flesh juice of medium viscosity and a low solid matter content. The juice addition allows to save some egg white. Furthermore, the time for beating the mixture is reduced in comparison to the time required with eggwhite alone. Guar gum or carob bean gum addition increases this effect. With adding powder sugar to the beaten eggwhite-juice mixture, a froth which can be baked, is obtained.

As stated hereinabove, the cocoa fruit flesh of preferably peeled cocoa fruits which may still contain the juice, can also be used as additive to food and for other purposes. The following examples serve to illustrate its use without, however, being limited thereto.

EXAMPLE 38

The cocoa fruit flesh obtained in Example 1 is comminuted and pulped into a paste-like consistency without being freed from the juice component thereof. To 1 kg. of this paste are added
3 kg. to 6 kg. of water,
1.2 kg. of sucrose, and
about 500 g. to 700 g. of citric acid.
Small amounts of artificial and/or natural flavor, for instance, strawberry flavor concentrate and coloring and also preservative agents are added. The resulting liquid composition may be carbonated and bottled as a beverage possessing a long shelf life or an alcoholic beverage may be added thereto to produce a cocktail.

EXAMPLE 39

A low-calorie dressing is made by combining 200 g. of finely comminuted cocoa fruit flesh still containing the juice therein with 400 g. of tomato paste, 10 drops of carotene color, and minor amounts of flavoring agents such as garlic, onion powder, oregano, and pepper. These ingredients are thoroughly mixed together, for instance, in a mixer or a colloid mill and there are added 100 cc. of invert sugar, or other non-crystallizable sugar derivatives as well as any desired preservative, flavoring agents, salt, mono-sodium glutamate, or the like. The resulting dressing can be used for salads, spreads, and the like. By replacing the 400 g. of tomato paste with a comparable amount of concentrated apple, peach, apricot or strawberry puree, a low-calorie pie filling and/or ice cream topping may also be prepared.

EXAMPLE 40

Soft Drink Base 140 g. of the finely comminuted parenchymatous tissue of the cocoa fruit,
40 g. of invert sugar,
20 g. of orange marmelade,
0.1 g. of yellow color for food products,
0.5 g. of sodium benzoate,
0.5 g. of potassium sorbate,
1.0 g. of imitation orange flavor, and
20 g. of water are intimately mixed with each other. The resulting soft drink base is supplied to bottlers, who will add water, if desired, sugar and carbon dioxide to produce a soft drink with orange flavor. Addition of orange marmelade fortifies the bitter orange aroma. Of course, in place of orange flavor and orange marmelade, there can be used any other type of fruit flavor with or without the addition of marmelade.

EXAMPLE 41

Low Calorie Italian Dressing 25 g. of olive oil,
250 g. of finely comminuted parenchymatous tissue of the cocoa fruit
10 g. of salt,
100 g. of vinegar,
5 g. of chopped onions,
5 g. of garlic powder,
1 g. of potassium sorbate,
1 g. of sodium benzoate, and
100 g. of water are thoroughly mixed in a string wire mixer. The mixture is homogenized in a homogenizer or a colloid mill.

In a similar manner there may be produced any other type of dressing with more or less oil or vinegar and with other components as required.

EXAMPLE 42

Pizza Base 250 g. of coarsely milled parenchymatous tissue of the cocoa fruit,
200 g. of tomato paste,
10 g. of anchovies,
10 g. of chopped capers,
5 g. of oregano,
25 g. of salt,
50 g. of invert sugar,
50 g. of soybean protein,
dash of thyme,
dash of celery, and
dash of black pepper
are thoroughly mixed with each other for about 10 minutes and the mixture is homogenized, if desired. The resulting paste is spread on the pizza dough before putting it into the pizza oven.

EXAMPLE 43

Meat Extender 250 g. of coarsely milled parenchymatous tissue of the cocoa fruit,
50 g. of vegetable protein such as soybean protein,
100 g. of finely minced meat, salt,
pepper,
food color,
preservative agents, and
meat aroma, such as hickory smoke aroma,
are thoroughly mixed and passed through an extruder. The mixture can be filled in sausage skins. Or it can be fried like Hamburgers or canned for later consumption.

In place of the meat there can also be used minced seafood, such as shrimps, crabs, and the like which are too small for canning and shipping.

EXAMPLE 44

Chocolate Dessert 225 g. of the parenchymatous tissue of the cocoa fruit,
50 g. of an edible oil,
150 g. of cocoa powder,
50 g. of inert sugar or sugar,
25 g. of whey powder or dry milk,
propyl p-hydroxy benzoate,
potassium sorbate, and
vanillin solution are thoroughly mixed with each other and placed into a freezer until served.

EXAMPLE 45

Cake Mixture 250 g. of wheat flour,
150 g. of sugar,
180 g. of the parenchymatous tissue of the cocoa fruit either in the coarsely milled state of finely comminuted,
2 eggs, and
50 g. of baking powder are thoroughly mixed with each other for 15 minutes. The mixture is filled into a baking mold or dish and is baked at about 175° C. A well tasting cake is produced.

EXAMPLE 46

Low Calorie Mayonnaise 200 g. of the parenchymatous tissue of the cocoa fruit and
200 g. of mayonnaise are intimately mixed with each other and thoroughly homogenized. The product can also be used as bread spread of a lower calorie value than mayonnaise as such.

EXAMPLE 47

Maccaroni 500 g. of semolina,
200 g. of the parenchymatous tissue of the cocoa fruit,
7.5 g. of salt, are intimately mixed with each other and the mixture is processes to maccaronis.

EXAMPLE 48

Maccaroni 500 g. of semolina,
250 g. of the parenchymatous tissue of the cocoa fruit,
7.5 g. of salt,
25 g. of soybean protein, are intimately mixed with each other and the mixture is processed to maccaroni.

EXAMPLE 49

Animal Feed Containing Molasses 100 kg. of partly dried cocoa fruit flesh which still contains about 50% of its juice,
50 kg. to 75 kg. of molasses 74 Brix, and
20 kg. to 40 kg. of soymeal are intimately mixed with each other and the mixture is heated to 60°–70° C. by spreading it on a conveyor belt and passing it through a heating chamber. Heating is continued until sufficient water is removed to permit pressing the mixture in a pelleting machine into pellets of a size which is accepted by the animal to which it is fed. In place of soybean meal, there can be used other oil seed residues. The oil seed residues may also be completely omitted.

EXAMPLE 50

1000 kg. of freshly harvested Theobroma fruits are placed in a vat containing 10,000 liters of a 5% aqueous solution of potassium sorbate. The mixture is gently stirred therein for about 30 minutes. The fruits are removed from the vat and are then kiln dried until they can be opened. After removal of the beans, the residual pods with the fruit flesh are ground and intimately mixed with 3 kg. of suet by repeatedly passing the mixture through a roller mill. The resulting mixture is a nutritious and tasty animal feed composition.

In place of potassium sorbate, there may be used other preservative agents such as 2% to 3% aqueous sodium or calcium hypochlorite or sodium or potassium disulfite solutions. Exposure of the fruits to a chlorine, sulfur dioxide, or formaldehyde containing atmosphere may also be employed. These preservatives may also be used in aqueous solution. Other suitable preservatives are, for instance, ozone in a very low concentration such as a 2 ml. per cu.m. of air, methyl formate, diphenyl, ammonia, sodium o-phenyl phenolate, nitrogen trichloride, and all preservatives and disinfectants used in processing fruit.

We claim:

1. In a method of improving the texture of food, beverages, and industrial products, the step of adding to such food, beverages or industrial products as texturizing agent an effective amount of an agent selected from the group consisting of the parenchymatous tissue of the cocoa fruit, the cocoa fruit juice removed therefrom, the hydrocolloid isolated from said cocoa fruit juice, and a mixture of said agents, said texturizing agent being intimately mixed with said food, beverages, or industrial products.

2. The method of claim 1, in which the texturizing agent is the purified cocoa fruit juice.

3. The method of claim 1, in which the texturizing agent is a very finely comminuted parenchymatous tissue of the cocoa fruit.

4. The method of claim 1, in which the texturizing agent is a dry hydrocolloid derivative of the cocoa fruit juice separated from the parenchymatous tissue of the cocoa fruits.

5. The method of claim 1, in which the texturizing agent is added to margarine.

6. The method of claim 1, in which the texturizing agent is added as binding agent for cigars and cut tobacco.

7. The method of claim 1, in which the texturizing agent is added to textile material as finishing agent so as to reduce friction resistance.

* * * * *